United States Patent
Ihatsu et al.

(10) Patent No.: US 11,904,110 B2
(45) Date of Patent: Feb. 20, 2024

(54) TRANSPERINEAL STEPPER INCLUDING A GEARLESS LINEAR MOVEMENT

(71) Applicant: KONINKLIJKE PHILIPS N.V., Eindhoven (NL)

(72) Inventors: Mika Tapani Ihatsu, Gainesville, FL (US); Olli Tapio Friman, Gainesville, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 822 days.

(21) Appl. No.: 16/616,571

(22) PCT Filed: May 30, 2018

(86) PCT No.: PCT/EP2018/064127
§ 371 (c)(1),
(2) Date: Nov. 25, 2019

(87) PCT Pub. No.: WO2018/219979
PCT Pub. Date: Dec. 6, 2018

(65) Prior Publication Data
US 2020/0155802 A1  May 21, 2020

Related U.S. Application Data

(60) Provisional application No. 62/512,746, filed on May 31, 2017.

(51) Int. Cl.
*A61M 25/01* (2006.01)
*A61B 8/12* (2006.01)
(Continued)

(52) U.S. Cl.
CPC .......... *A61M 25/0113* (2013.01); *A61B 8/12* (2013.01); *A61B 8/4209* (2013.01); *A61B 90/50* (2016.02);
(Continued)

(58) Field of Classification Search
CPC . A61B 18/12; A61B 8/42–4209; A61B 90/50; A61B 1/00149; A61B 1/31;
(Continued)

(56) References Cited

U.S. PATENT DOCUMENTS 3,349,777 A * 10/1967 Wallace .................. A24C 1/30
131/59
4,865,313 A    9/1989 Kuo
(Continued)

FOREIGN PATENT DOCUMENTS

DE    102010045395 A1    3/2012
JP       2012036942 A    2/2012

OTHER PUBLICATIONS

International Search Report and Written Opinion From PCT/EP2018/064127 dated Sep. 14, 2018.

*Primary Examiner* — Keith M Raymond
*Assistant Examiner* — Fikirte (Fiki) T Ashine
(74) *Attorney, Agent, or Firm* — Sherry Austin (57) ABSTRACT

A device includes a medical instrument mounting structure; a base; and a gearless longitudinal translation device connected to and enabling longitudinal movement of the medical instrument mounting structure with respect to the base. The gearless longitudinal translation device includes: a first friction wheel having at least a first beveled side surface, and a second friction wheel having at least a second beveled surface; a first linear rod disposed between the first and second friction wheels and in contact with the first and second beveled surfaces; and a control mechanism attached to the first and second friction wheels for rotating the first and second friction wheels. Rotation of the first and second friction wheels causes a longitudinal displacement of the first linear rod with respect to the first and second friction wheels, which in turn causes the medical instrument mount-
(Continued)

ing structure to be longitudinally displaced with respect to the base.

20 Claims, 9 Drawing Sheets

(51) Int. Cl.
    *A61B 8/00*         (2006.01)
    *A61B 90/50*       (2016.01)
    *A61B 1/31*         (2006.01)
    *A61B 17/00*       (2006.01)
    *A61B 1/00*         (2006.01)

(52) U.S. Cl.
    CPC ............. *A61B 1/00149* (2013.01); *A61B 1/31* (2013.01); *A61B 2017/00398* (2013.01)

(58) Field of Classification Search
    CPC .. A61B 2017/00398; A61B 2017/3409; A61B 17/3403–05; A61M 25/0113
    See application file for complete search history.

(56) References Cited

U.S. PATENT DOCUMENTS

| | | | |
|---|---|---|---|
| 5,871,448 A * | 2/1999 | Ellard | A61B 8/0841 600/459 |
| 5,931,786 A | 8/1999 | Whitmore | |
| 2003/0014039 A1 | 1/2003 | Barzell et al. | |
| 2006/0041245 A1 * | 2/2006 | Ferry | A61B 90/50 604/95.01 |
| 2013/0209208 A1 * | 8/2013 | Bailey | B25J 9/1065 414/728 |
| 2017/0030867 A1 | 2/2017 | Facuher | |

\* cited by examiner

TRANSPERINEAL STEPPER INCLUDING A GEARLESS LINEAR MOVEMENT

CROSS REFERENCE TO RELATED APPLICATIONS

This application is a U.S. national phase application of International Application No. PCT/EP2018/064127 filed on May 30, 2018, which claims the benefit of U.S. Provisional Application Serial No 62/512,746 filed on May 31, 2017 and is incorporated herein by reference.

BACKGROUND

A transperineal stepper is a device which may be employed to drive a biopsy needle through an intended location of the perineum (i.e., the area between the anus and the scrotum or vulva of a patient). The transperineal stepper includes an acoustic (e.g., ultrasound) probe which is insertable into the rectum of the patient, and allows the acoustic probe to be rotated to various angles during a procedure.

One key feature in a transperineal stepper is the acoustic probe's linear movement in and out of the patient (herein referred to as a longitudinal direction).

Inherently, a longitudinal translation mechanism in a transperineal stepper which provides for the linear movement of the acoustic probe in and out of the patient involves moving parts.

However, such mechanisms with moving parts are often very difficult to clean and keep clean, which is problematic for a transperineal stepper used in a clean and partially sterile environment.

Therefore, a transperineal stepper is needed which includes a longitudinal translation mechanism for linear movement of an acoustic probe and which can relatively easily be cleaned and kept clean when operating in a clean and partially sterile environment.

SUMMARY

According to an aspect of the present disclosure, a transperineal stepper includes: an acoustic probe including a first end which is insertable into a patient; a probe mounting structure which holds the acoustic probe; a base; and a gearless longitudinal translation device connected to, and enabling longitudinal movement of, the probe mounting structure and the acoustic probe with respect to the base. The gearless longitudinal translation device comprises: a first friction wheel having at least a first beveled side surface, and a second friction wheel having at least a second beveled surface; and a first linear rod disposed between the first and second friction wheels and in contact with the first and second beveled surfaces, wherein a displacement of the first linear rod longitudinally with respect to the first and second friction wheels causes the acoustic probe and the probe mounting structure to be longitudinally displaced with respect to the base.

In some embodiments, the transperineal stepper of claim 1 further comprises an axle connecting the first friction wheel and second friction wheel, and a bearing disposed in contact with the axle at a side of the axle which is opposite the first linear rod, wherein the bearing applies a force to the first and second friction wheels to push the first and second friction wheels against the first linear rod.

In some variations of these embodiments, the bearing is pressed by a spring force against the axle.

In some embodiments, the gearless longitudinal translation device further comprises: a third friction wheel having at least a third beveled surface, and a fourth friction wheel having at least a fourth beveled surface; a second linear rod disposed between the third and fourth friction wheels and in contact with the third and fourth beveled surfaces; and a coupling element coupling the second friction wheel to the third friction wheel.

In some variations of these embodiments, the transperineal stepper further comprises: a first axle connecting the first friction wheel and second friction wheel; a second axle connecting the third friction wheel and fourth friction wheel; a first bearing disposed in contact with the first axle at a side of the first axle which is opposite the first linear rod, wherein the first bearing applies a first force to the first and second friction wheels to push the first and second friction wheels against the first linear rod; and a second bearing disposed in contact with the second axle at a side of the second axle which is opposite the second linear rod, wherein the second bearing applies a second force to the third and fourth friction wheels to push the third and fourth friction wheels against the second linear rod.

In some variations of these embodiments, the first bearing is pressed by a first spring force against the first axle, and the second bearing is pressed by a second spring force against the second axle.

In some embodiments, the first linear rod is cylindrical, the first linear rod is made of stainless steel or titanium, and the first and second frictions wheels are made of stainless steel or titanium.

In some embodiments, the transperineal stepper further comprises a knob connected to at least ne of the first and second friction wheels, wherein when the knob is rotated, the first linear rod is displaced longitudinally with respect to the first and second friction wheels, causing the acoustic probe and probe mounting structure to be longitudinally displaced with respect to the base.

In some variations of these embodiments, the first linear rod is fixed to the base, the acoustic probe and probe mounting structure are connected to the first and second friction wheels, and rotation of the knob causes the first and second friction wheels to rotate and move longitudinally with respect to the first linear rod and the base, in turn causing the acoustic probe and the probe mounting structure to move longitudinally with respect to the base.

In some variations of these embodiments, the first and second friction wheels are fixed longitudinally with respect to the base, and rotation of the knob causes the first and second friction wheels to rotate and further causes the first linear rod to move longitudinally with respect to the first and second friction wheels and the base, in turn causing the acoustic probe and the probe mounting structure to move longitudinally with respect to the base.

According to another aspect of the present disclosure, a device comprises: a medical instrument mounting structure; a base; and a gearless longitudinal translation device connected to, and enabling longitudinal movement of, the medical instrument mounting structure with respect to the base. The gearless longitudinal translation device comprises: a first friction wheel having at least a first beveled side surface, and a second friction wheel having at least a second beveled surface; a first linear rod disposed between the first and second friction wheels and in contact with the first and second beveled surfaces; and a control mechanism attached to at least one of the first and second friction wheels for rotating the first and second friction wheels, wherein rotation of the first and second friction wheels causes a displacement of the first linear rod longitudinally with respect to the first and second friction wheels, which in turn causes the medical instrument mounting structure to be longitudinally displaced with respect to the base.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms "a", "an" and "the" are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Figure 1:
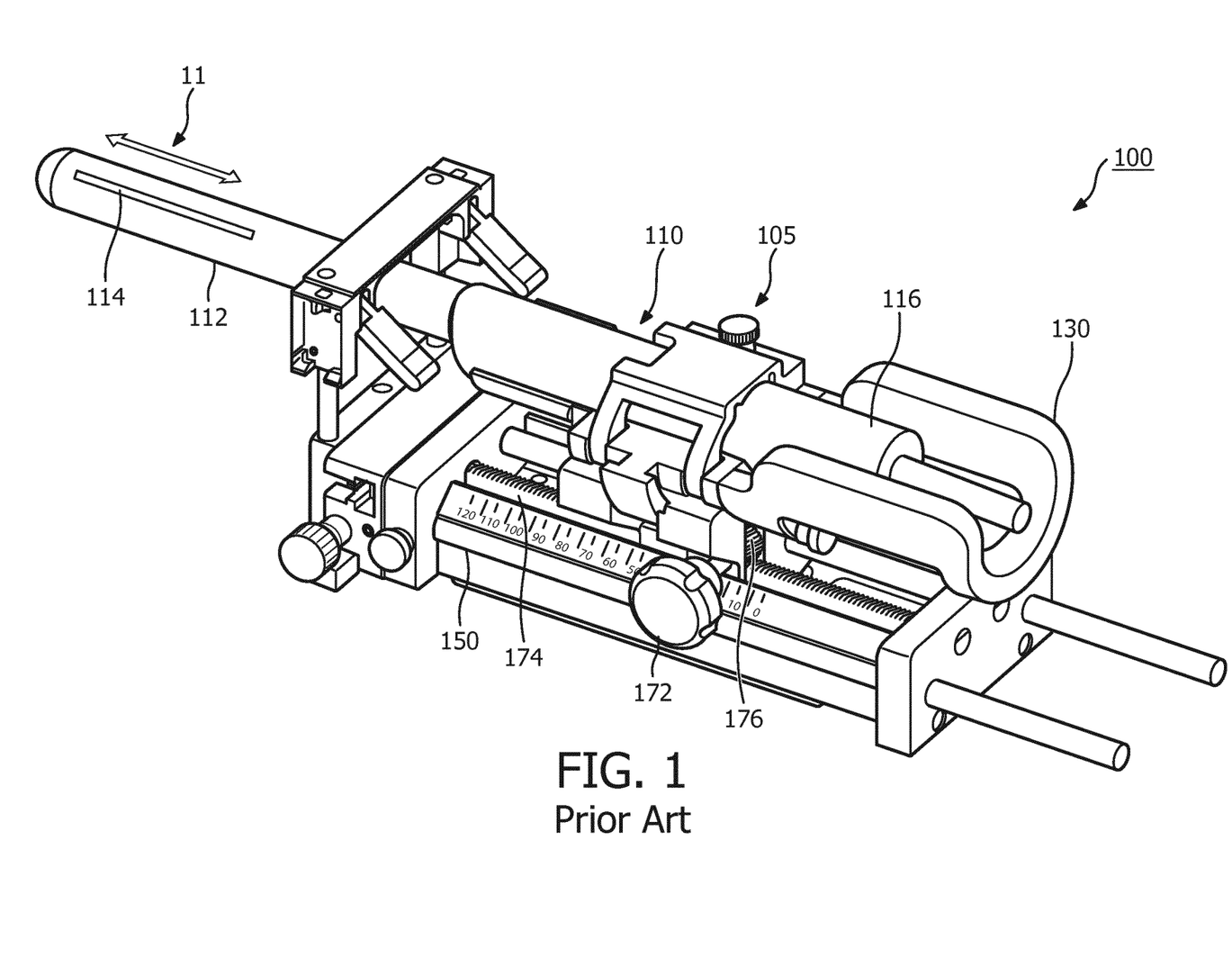
FIG. 1 is a perspective view of a system including a transperineal stepper with an acoustic probe and a cradle and a longitudinal translation mechanism for the linear movement of the acoustic probe in and out of a patient.

To explain in more detail issues which may be raised in maintaining the cleanliness of a longitudinal translation mechanism of a transperineal stepper, FIG. 1 is a perspective view of an example transperineal stepper system 100, including a transperineal stepper 105, having an acoustic (e.g., ultrasound) probe 110 positioned in a cradle 130 serving as probe mounting structure which holds acoustic probe 110, and a base 150.

Acoustic probe 110 includes an elongated neck 112, at least one acoustic transducer 114 connected to a distal end of the elongated neck 112, and an elongated body 116 connected to a proximal end of the elongated neck 112.

Acoustic probe 110 is configured to move longitudinally for insertion in the rectum of the patient, and to rotate through operation of the cradle 130 for obtaining images at different angles from within the patient's body.

The linear movement of acoustic probe 110 into and out of the patient's body (e.g., via the patient's rectum) in a longitudinal direction 11 is achieved by means of a knob 172 which is connected to a gear spur 176 which engages a gear rack 174. Acoustic probe 110 and cradle 130 are also connected to gear spur 176 so as to be transported in longitudinal direction 11 as gear spur 176 moves longitudinally along gear rack 174.

However, it should be apparent that gear spur 176 and gear rack 174, each having a large number of "teeth" is in general very difficult to clean and keep clean, which is problematic for a device used in a clean and partially sterile environment.

So a different longitudinal translation mechanism which may be easier to clean and keep clean is desired.

Figure 2:
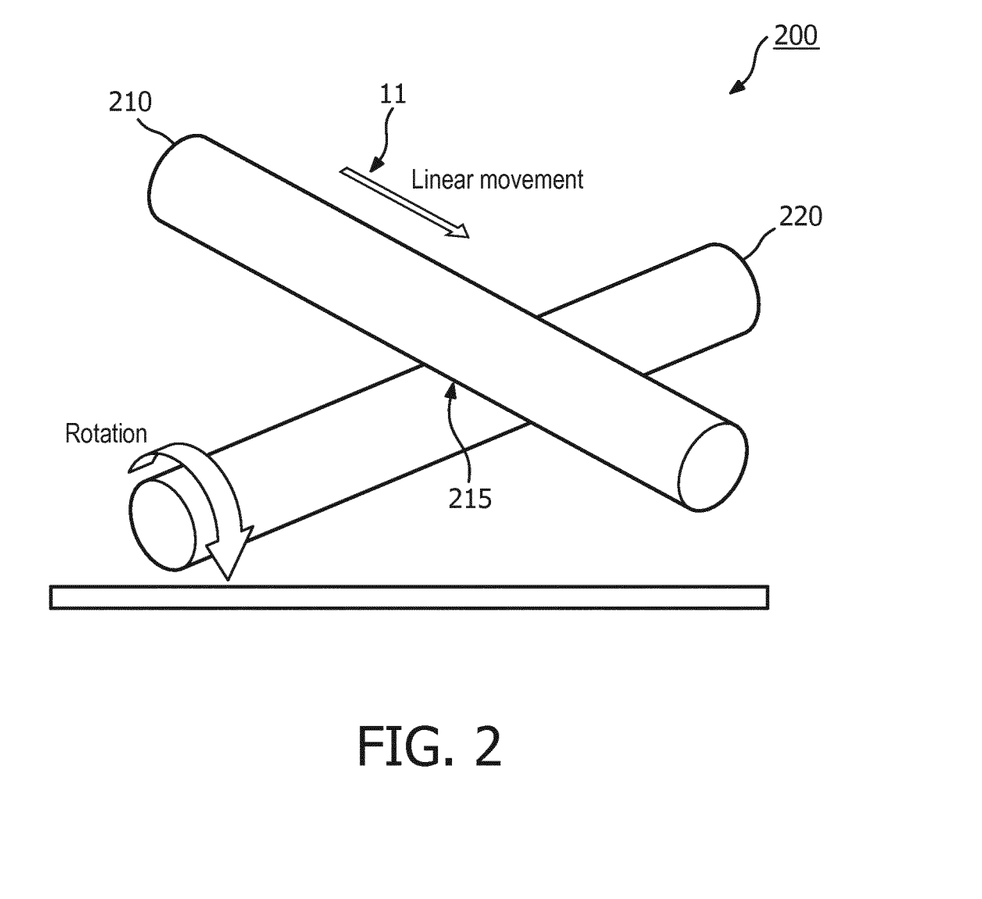
FIG. 2 illustrates an arrangement which may be employed to produce linear movement.

FIG. 2 illustrates an arrangement 200 which may be employed to produce linear movement. Arrangement 200 replaces the spur gear and gear rack of the longitudinal transport mechanism of FIG. 1 with a linear rod 210 and a smooth wheel 220. Here, wheel 220 may be rotated by means of a knob (not shown) such as knob 172 of FIG. 1. The knob's rotation force, which is transferred to linear rod 210 by its mechanical shape, is replaced by friction. To generate enough friction, at least one material, and beneficially both materials, of linear rod 210 and wheel 220 should be a hard material, with a high coefficient of friction to generate enough surface pressure to transfer rotation force from wheel 220 securely to the linear movement of linear rod 210.

To increase the friction of arrangement 200, a friction wheel with a beveled or cone-shaped surface may be employed with the linear rod.

Figure 3A:
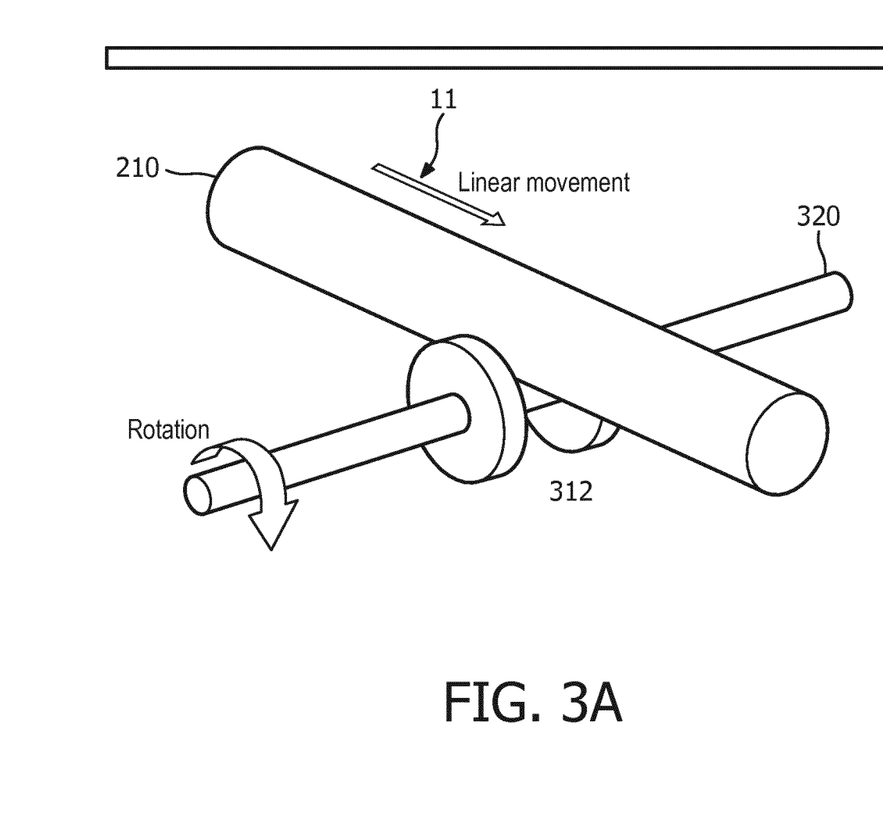
FIG. 3A shows a perspective view and FIG. 3B shows an end view of a gearless longitudinal translation device.
Figure 3B:
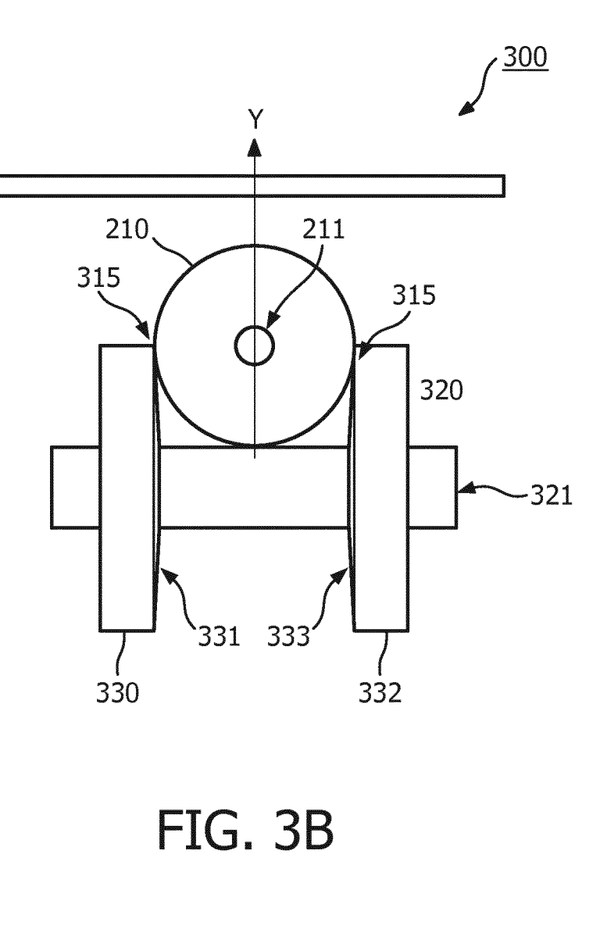

FIG. 3A shows a perspective view and FIG. 3B shows an end view of a gearless longitudinal translation device 300 which may employ principles of arrangement 200, and supply increased friction for more efficient linear translation of linear rod 210. Gearless longitudinal translation device 300 includes: a first friction wheel 330 having at least a first beveled or cone-shaped side surface 331; a second friction wheel 332 having at least a second beveled or cone-shaped side surface 333; and linear rod 210 disposed between the first and second friction wheels 330 and 332 and in contact with first and second beveled side surfaces 331 and 333. An axle 320 connects first friction wheel 330 and second friction wheel 332 to each other. In device 300, because of beveled or cone-shaped side surfaces 331 and 333, even minimal push force generates enormous surface pressure at friction points 315, which may provide a tight mechanical connection and more efficient linear movement of linear rod 210 in longitudinal direction 11.

Beneficially, each of first and second beveled side surfaces 331 and 333 may be beveled at an angle Δ (see FIG. 5) of less than 5 degrees, and even more beneficially between 0.5 and 3 degrees with respect to a direction (labeled in FIG. 3 as the "Y" direction) which is normal to the central axis 321 of axle 320 and which passes through central axis 211 of linear rod 210. In other words, first and second beveled side surfaces 331 and 333 may be beveled at an angle Δ with respect to planar.

Beneficially, linear rod 210 may be cylindrical, linear rod 210 may be made of stainless steel or titanium, and first and second frictions wheels 330 and 332 are made of stainless steel or titanium. In other embodiments, linear rod 210 may have a different shape other than cylindrical, for example a rectangular cross section.

Figure 4:
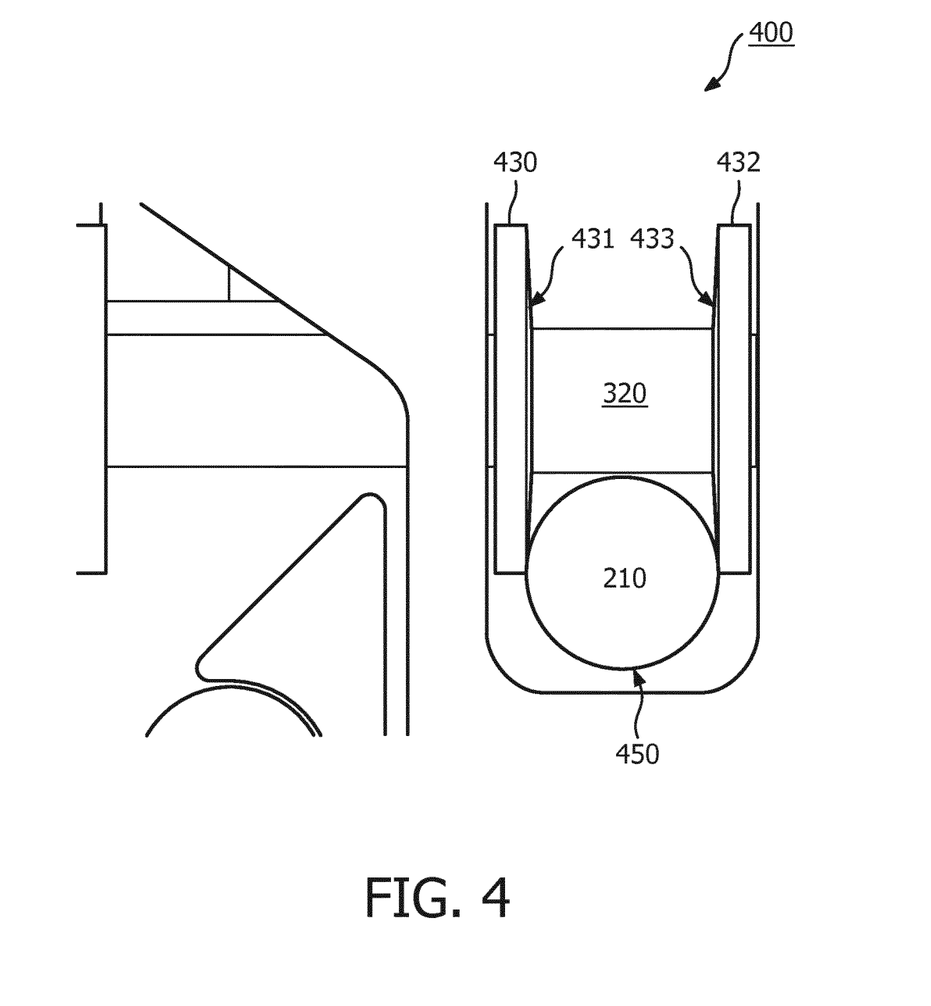
FIG. 4 shows one embodiment of a gearless longitudinal translation device.

FIG. 4 shows one embodiment of a gearless longitudinal translation device 400 which may be adapted for use in a transperineal stepper. Gearless longitudinal translation device 400 includes: a first friction wheel 430 having at least a first beveled or cone-shaped side surface 431; a second friction wheel 432 having at least a second beveled or cone-shaped side surface 433; and linear rod 210 disposed between the first and second friction wheels 430 and 432 and in contact with first and second beveled side surfaces 431 and 433. Axle 320 connects first friction wheel 430 and second friction wheel 432 to each other.

Here, a bearing 450 applies a force to linear rod 210 to press linear rod 210 against first and second friction 430 and 432, and in particular against beveled side surfaces 431 and 433, to ensure a tight mechanical connection and more efficient linear movement of linear rod 210 in longitudinal direction 11.

Although not shown in FIG. 4, the device may further include one or more knobs such as knob 172 of FIG. 1 for rotating axle 320 and first and second friction wheels 430 and 432.

Beneficially, each of first and second beveled surfaces 431 and 433 may be beveled at an angle Δ (see FIG. 5) of less than 5 degrees, and even more beneficially between 0.5 and 3 degrees with respect to a direction (labeled in FIG. 5 as the "Y" direction) which is normal to the central axis 321 of axle 320 and which passes through central axis 211 of linear rod 210. In other words, first and second beveled surfaces 431 and 433 may be beveled at an angle Δ with respect to planar.

In some embodiments, first and second friction wheels 430 and 432 may be mounted in a fixed longitudinal relationship to a base of a transperineal stepper, and the rotation of first and second friction wheels 430 and 432 by means of the knob(s) may cause linear rod 210 to move in a longitudinal direction. Meanwhile, linear rod 210 may be attached or connected to an acoustic probe or medical instrument having a first end which is insertable into a patient, and a probe or medical instrument mounting structure which holds the acoustic probe or medical instrument. Longitudinal movement of linear rod 210 may in turn cause longitudinal movement or displacement of the acoustic probe (or medical instrument) and probe (or medical instrument) mounting structure so as to insert and retract the acoustic probe (or medical instrument) from a patient (e.g., the rectum of the patient).

Figure 5:
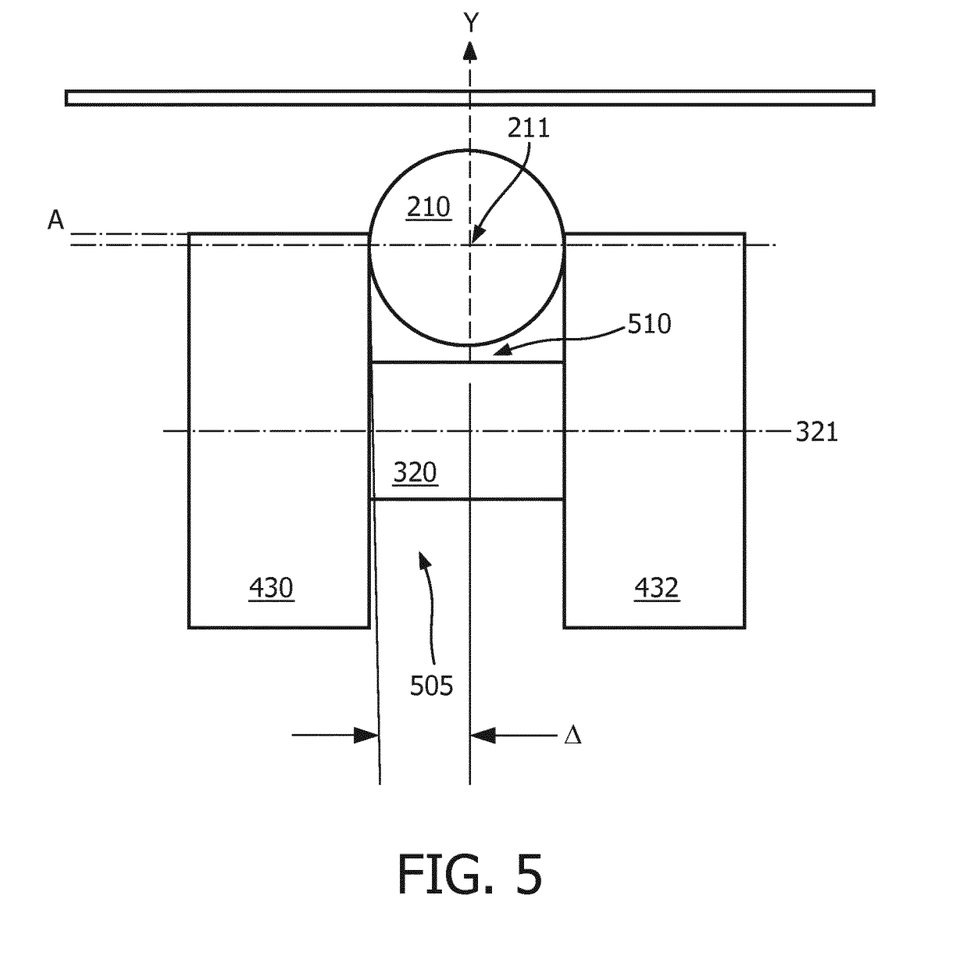
FIG. 5 illustrates a beneficial relationship between a linear rod and first and second friction wheels.

FIG. 5 illustrates a beneficial relationship between linear rod 210 and first and second friction wheels 430 and 432. In particular, FIG. 5 illustrates that it is beneficial if central axis 211 of linear rod 210 is disposed within a channel 505 defined between first and second friction wheels 430 and 432. In other words, beneficially a "top" portion of each of first and second friction wheels 430 and 432 extends beyond the axis of linear rod 210 by an amount "A" as shown in FIG. 5. Additionally, a clearance 510 is provided between linear rod 210 and axle 320.

Figure 6:
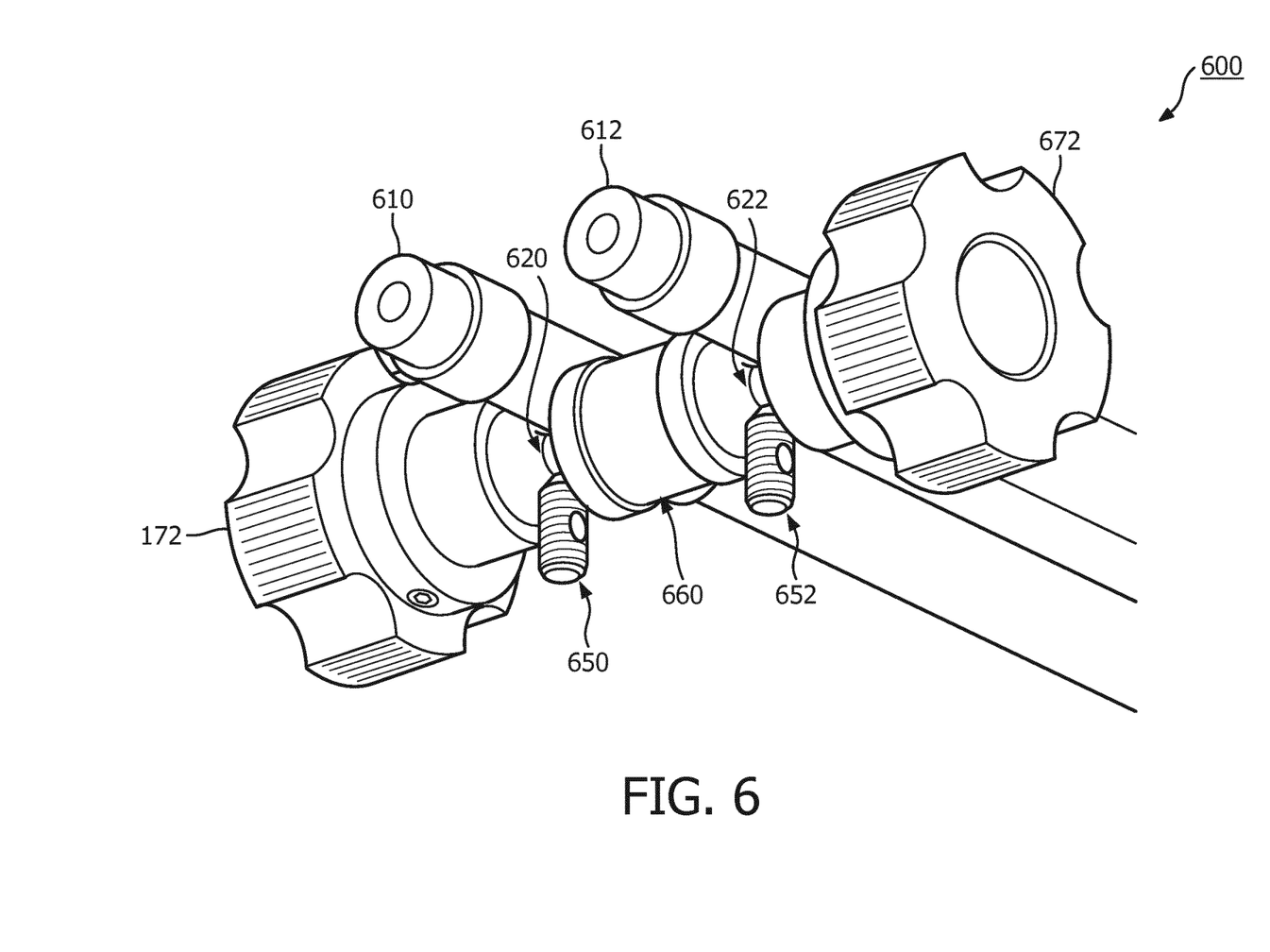
FIG. 6 shows a perspective view of another embodiment of a gearless longitudinal translation device.
Figure 7:
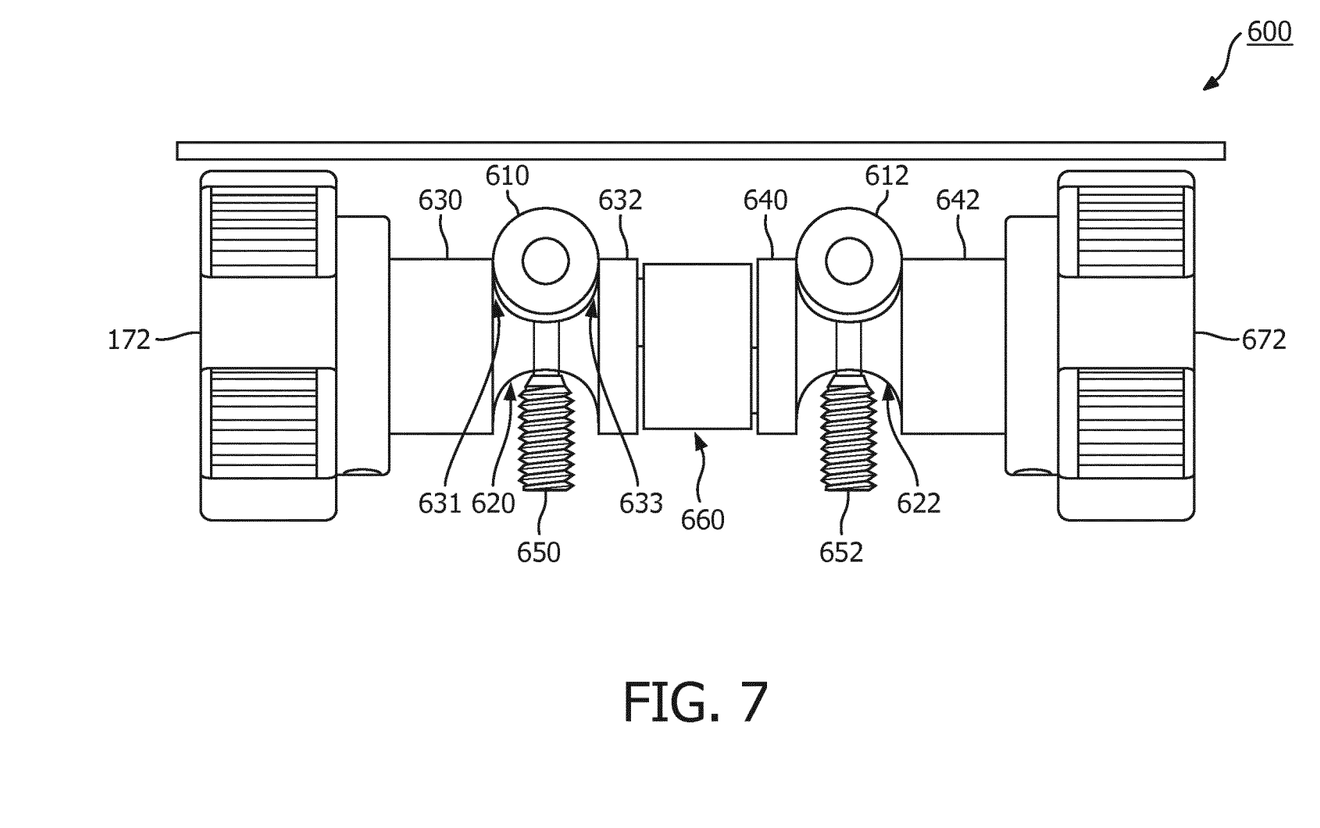
FIG. 7 shows an end view of another embodiment of a gearless longitudinal translation device.

FIG. 6 shows a perspective view and FIG. 7 shows an end view of another embodiment of a gearless longitudinal translation device 600.

Gearless longitudinal translation device 600 includes: a first friction wheel 630 having at least a first beveled or cone-shaped side surface 631; a second friction wheel 632 having at least a second beveled or cone-shaped side surface 633; and a first linear rod 610 disposed between the first and second friction wheels 630 and 632 and in contact with the first and second beveled side surfaces 631 and 633. A first axle 620 connects first friction wheel 630 and second friction wheel 632 to each other.

Gearless longitudinal translation device 600 also includes: a third friction wheel 640 having at least a third beveled or cone-shaped side surface; a fourth friction wheel 642 having at least a fourth beveled or cone-shaped side surface; and a second linear rod 612 disposed between the third and fourth friction wheels 640 and 642 and in contact with the third and fourth beveled side surfaces. A second axle 622 connects third friction wheel 640 and fourth friction wheel 642 to each other.

Beneficially, each of first, second, third and fourth beveled side surfaces may be beveled at an angle Δ (see FIG. 5) of less than 5 degrees, and even more beneficially between 0.5 and 3 degrees with respect to a direction (labeled in FIG. 3B and FIG. 5 as the "Y" direction) which is normal to the central axis of the axles. In other words, first, second, third and fourth beveled side surfaces may be beveled at an angle Δ with respect to planar.

Gearless longitudinal translation device 600 also includes a coupling element 660 which connects or couples second friction wheel 632 to third friction wheel 640. Beneficially, each of friction wheels 630, 632, 640 and 642 can freely centralize. Accordingly, each of friction wheels 630, 632, 640 and 642 are provided as individual parts, and they may be synchronized in the center by coupling element 660.

Gearless longitudinal translation device 600 also includes a first bearing (e.g., a ball) 650 and a second bearing (e.g., a ball) 652. First bearing 650 is disposed in contact with first axle 620 at a side of first axle 620 which is opposite first linear rod 610 and is configured to apply a force to first and second friction wheels 630 and 632 to push first and second friction wheels 630 and 632 against first linear rod 610. Second bearing 652 is disposed in contact with second axle 622 at a side of second axle 622 which is opposite second linear rod 612 and is configured to apply a force to third and fourth friction wheels 640 and 642 to push third and fourth friction wheels 640 and 642 against second linear rod 622. Beneficially, first bearing 650 and second bearing 652 are spring-loaded bearings which are configured to be pressed by a spring force against first axle 620 and second axle 622, respectively.

Beneficially, each of the first and second linear rods 610 and 612 may be cylindrical, first and second linear rods 610 and 612 may be made of stainless steel or titanium, and first, second, third and fourth frictions wheels 630, 632, 640 and 642 are made of stainless steel or titanium. In other embodiments, first and second linear rods 610 and 612 may have a different shape other than cylindrical, for example a rectangular cross section.

In device 600, because of beveled or cone-shaped surfaces 631 and 633 and spring loaded bearings 650 and 652, even minimal push force generates enormous surface pressure at friction points 615, which may provide a tight mechanical connection and more efficient linear movement of first and second linear rods 610 and 612 in longitudinal direction 11.

Figure 8:
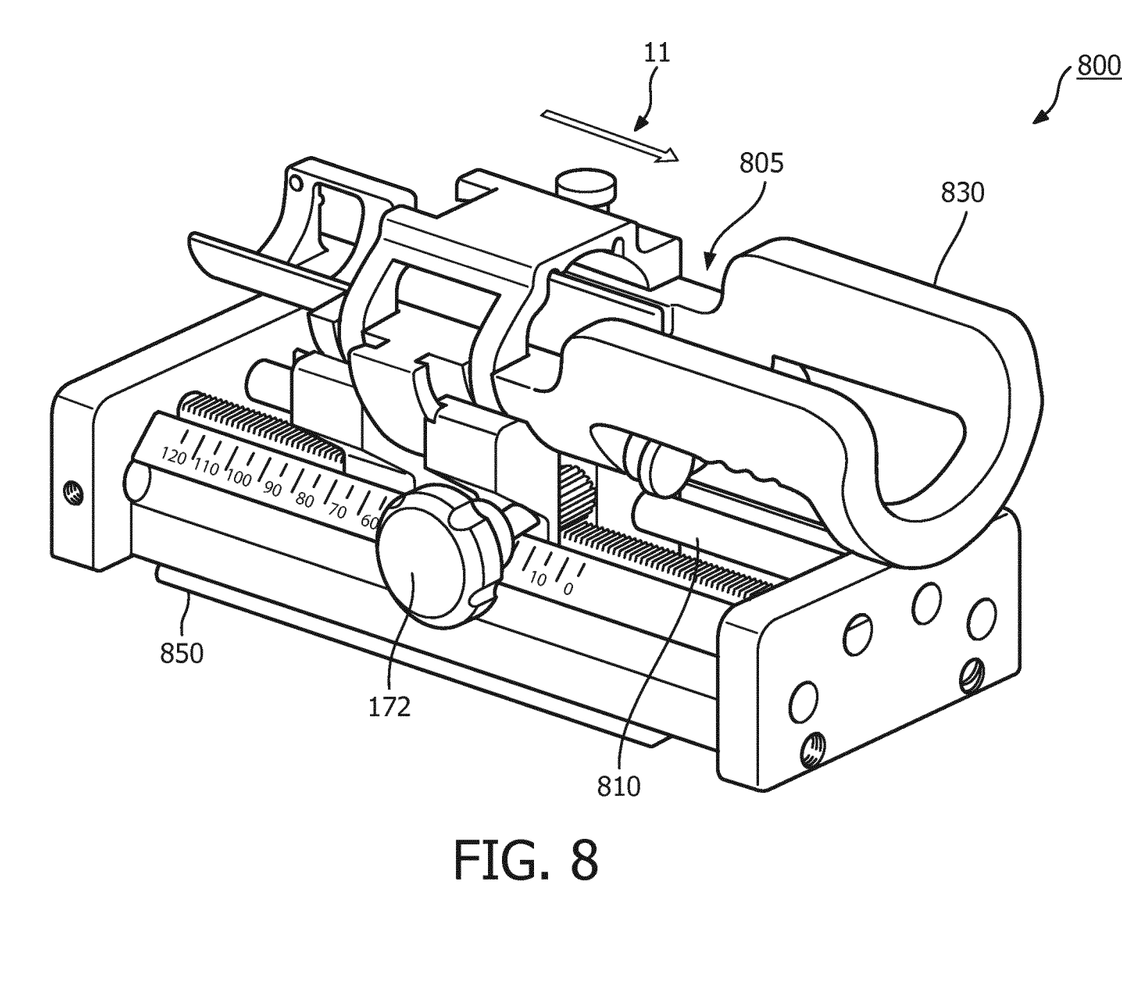
FIG. 8 illustrates a first embodiment of a transperineal stepper system including a transperineal stepper which may include a gearless longitudinal translation device.

FIG. 8 illustrates a first embodiment of a transperineal stepper system 800 including a transperineal stepper 805 which may include a gearless longitudinal translation device as described above with respect to FIGS. 3-7. In transperineal stepper system 800, a first linear rod 810 is fixed to a base 850, and an acoustic probe (not shown) and a probe mounting structure 830 are connected to the first and second friction wheels (not shown). Rotation of knob 172 and/or knob 672 (not shown in FIG. 8) causes the first and second friction wheels to rotate and move longitudinally with respect to the first linear rod and base 850, in turn causing the acoustic probe and probe mounting structure 830 to move longitudinally with respect to base 850. Thus the acoustic probe may be longitudinally displaced and thereby inserted in and retracted from a patient (e.g., a rectum of a patient).

Figure 9:
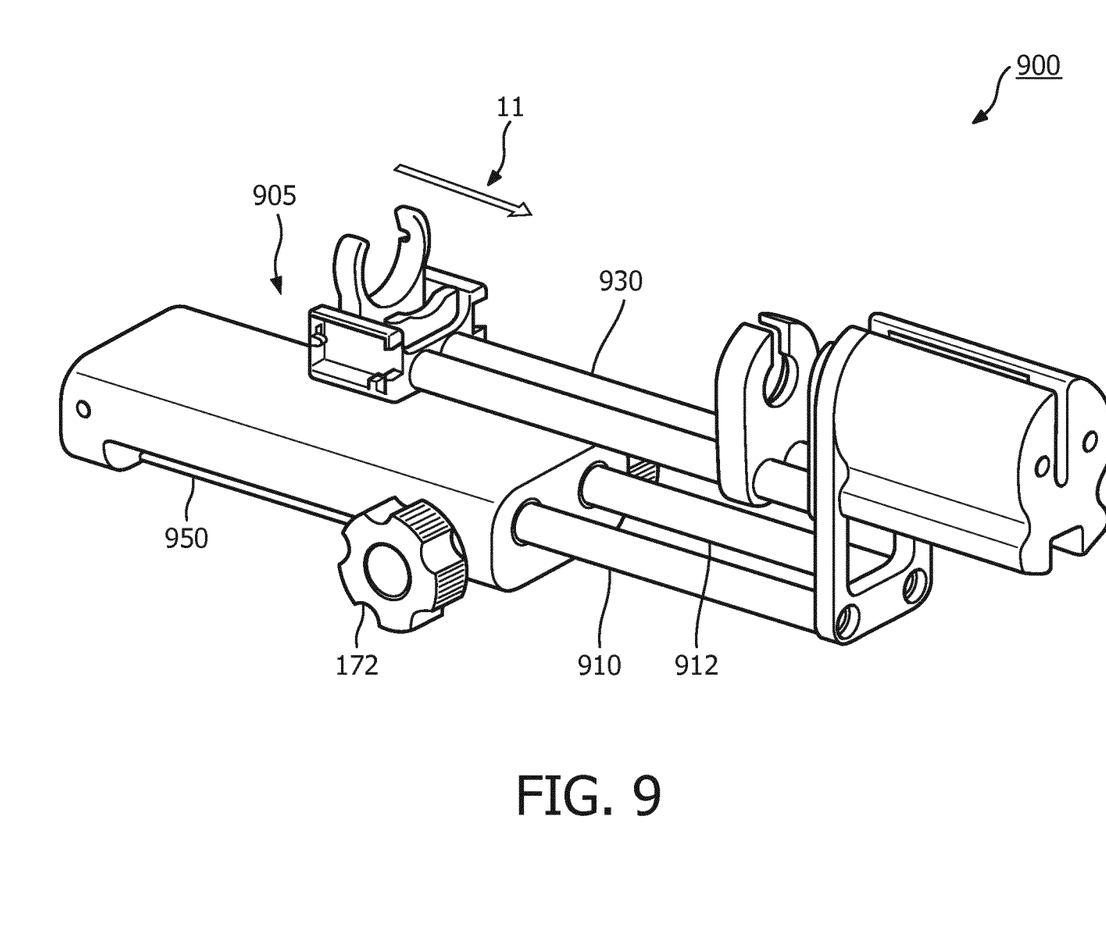
FIG. 9 illustrates a second embodiment of a transperineal stepper system including a transperineal stepper which may include a gearless longitudinal translation device.

FIG. 9 illustrates a second embodiment of a transperineal stepper system 900 including a transperineal stepper 905 which may include a gearless longitudinal translation device as described above with respect to FIGS. 3-7. In transperineal stepper system 900, the first and second friction wheels (not shown) are fixed longitudinally with respect to a base 950, and an acoustic probe (not shown) and a probe mounting structure 930 are connected to first and second linear rods 910 and 912. Rotation of knob 172 and/or knob 672 (not shown in FIG. 8) causes the first and second friction wheels to rotate and further causes first and second linear rods 910 and 912 to move longitudinally with respect to the first and second friction wheels and base 950, in turn causing the acoustic probe and probe mounting structure 930 to move longitudinally with respect to base 950. Thus the acoustic probe may be longitudinally displaced and thereby inserted in and retracted from a patient (e.g., a rectum of a patient).

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, although embodiments described above pertain specifically to transperineal stepper systems which include a probe mounting structure for longitudinally translating an acoustic probe mounted in the probe mounting structure, in general gearless longitudinal translation devices as described above may be applied to more general devices, which include a general medical instrument mounting structure and a base and which are configured to move a medical instrument or device into and out of a patient.

Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A transperineal stepper, comprising:
   an acoustic probe including a first end which is insertable into a patient;
   a probe mounting structure which holds the acoustic probe;
   a base; and
   a gearless longitudinal translation device connected to, and enabling longitudinal movement of, the probe mounting structure and the acoustic probe with respect to the base, wherein the gearless longitudinal translation device comprises:
   a first friction wheel having at least a first beveled side surface, and a second friction wheel having at least a second beveled surface; and
   a first linear rod disposed between the first and second friction wheels and in contact with the first and second beveled surfaces,
   wherein a displacement of the first linear rod longitudinally with respect to the first and second friction wheels causes the acoustic probe and the probe mounting structure to be longitudinally displaced with respect to the base.

2. The transperineal stepper of claim 1, further comprising an axle connecting the first friction wheel and second friction wheel, and a bearing disposed in contact with the axle at a side of the axle which is opposite the first linear rod, wherein the bearing applies a force to the first and second friction wheels to push the first and second friction wheels against the first linear rod.

3. The transperineal stepper of claim 2, wherein the bearing is pressed by a spring force against the axle.

4. The transperineal stepper of claim 1, wherein the gearless longitudinal translation device further comprises:
   a third friction wheel having at least a third beveled surface, and a fourth friction wheel having at least a fourth beveled surface;
   a second linear rod disposed between the third and fourth friction wheels and in contact with the third and fourth beveled surfaces; and
   a coupling element coupling the second friction wheel to the third friction wheel.

5. The transperineal stepper of claim 4, further comprising:
   a first axle connecting the first friction wheel and second friction wheel;
   a second axle connecting the third friction wheel and fourth friction wheel;
   a first bearing disposed in contact with the first axle at a side of the first axle which is opposite the first linear rod, wherein the first bearing applies a first force to the first and second friction wheels to push the first and second friction wheels against the first linear rod; and
   a second bearing disposed in contact with the second axle at a side of the second axle which is opposite the second linear rod, wherein the second bearing applies a second force to the third and fourth friction wheels to push the third and fourth friction wheels against the second linear rod.

6. The transperineal stepper of claim 5, wherein the first bearing is pressed by a first spring force against the first axle, and the second bearing is pressed by a second spring force against the second axle.

7. The transperineal stepper of claim 1, wherein the first linear rod is cylindrical, the first linear rod is made of stainless steel or titanium, and the first and second friction wheels are made of stainless steel or titanium.

8. The transperineal stepper of claim 1, further comprising a knob connected to at least one of the one of the first and second friction wheels, wherein when the knob is rotated, the first linear rod is displaced longitudinally with respect to the first and second friction wheels, causing the acoustic probe and the probe mounting structure to be longitudinally displaced with respect to the base.

9. The transperineal stepper of claim 8, wherein the first linear rod is fixed to the base, the acoustic probe and probe mounting structure are connected to the first and second friction wheels, and wherein rotation of the knob causes the first and second friction wheels to rotate and move longitudinally with respect to the first linear rod and the base, in turn causing the acoustic probe and the probe mounting structure to move longitudinally with respect to the base.

10. The transperineal stepper of claim 8, wherein the first and second friction wheels are fixed longitudinally with respect to the base, and wherein rotation of the knob causes the first and second friction wheels to rotate and further causes the first linear rod to move longitudinally with respect to the first and second friction wheels and the base, in turn causing the acoustic probe and the probe mounting structure to move longitudinally with respect to the base.

11. A device, comprising:
    a medical instrument mounting structure;
    a base; and
    a gearless longitudinal translation device connected to, and enabling longitudinal movement of, the medical instrument mounting structure with respect to the base, wherein the gearless longitudinal translation device comprises:
    a first friction wheel having at least a first beveled side surface, and a second friction wheel having at least a second beveled surface;
    a first linear rod disposed between the first and second friction wheels and in contact with the first and second beveled surfaces; and
    a control mechanism attached to at least one of the the first and second friction wheels for rotating the first and second friction wheels, wherein rotation of the first and second friction wheels causes a displacement of the first linear rod longitudinally with respect to the first and second friction wheels, which in turn causes the medical instrument mounting structure to be longitudinally displaced with respect to the base.

12. The device of claim 11, further comprising an axle connecting the first friction wheel and second friction wheel, and a bearing disposed in contact with the axle at a side of the axle which is opposite the first linear rod, wherein the bearing applies a force to the first and second friction wheels to push the first and second friction wheels against the first linear rod.

13. The device of claim 12, wherein the bearing is pressed by a spring force against the axle.

14. The device of claim 11, wherein the gearless longitudinal translation device further comprises:
- a third friction wheel having at least a third beveled surface, and a fourth friction wheel having at least a fourth beveled surface;
- a second linear rod disposed between the third and fourth friction wheels and in contact with the third and fourth beveled surfaces; and
- a coupling element coupling the second friction wheel to the third friction wheel.

15. The device of claim 14, further comprising:
- a first axle connecting the first friction wheel and second friction wheel;
- a second axle connecting the third friction wheel and fourth friction wheel;
- a first bearing disposed in contact with the first axle at a side of the first axle which is opposite the first linear rod, wherein the first bearing applies a first force to the first and second friction wheels to push the first and second friction wheels against the first linear rod; and
- a second bearing disposed in contact with the second axle at a side of the second axle which is opposite the second linear rod, wherein the second bearing applies a second force to the third and fourth friction wheels to push the third and fourth friction wheels against the second linear rod.

16. The device of claim 15, wherein the first bearing is pressed by a first spring force against the first axle, and the second bearing is pressed by a second spring force against the second axle.

17. The device of claim 11, wherein the first linear rod is cylindrical, the first linear rod is made of stainless steel or titanium, and the first and second frictions wheels are made of stainless steel or titanium.

18. The device of claim 11, wherein the control mechanism comprises a knob connected to the at least one of the first and second friction wheels, wherein when the knob is rotated, the first linear rod is displaced longitudinally with respect to the first and second friction wheels, causing the medical instrument mounting structure to be longitudinally displaced with respect to the base.

19. The device of claim 18, wherein the first linear rod is fixed to the base, the medical instrument mounting structure are connected to the first and second friction wheels, and wherein rotation of the knob causes the first and second friction wheels to rotate and move longitudinally with respect to the base, in turn causing the medical instrument mounting structure to move longitudinally with respect to the base.

20. The device of claim 18, wherein the first and second friction wheels are fixed longitudinally with respect to the base, and wherein rotation of the knob causes the first and second friction wheels to rotate and further causes the first linear rod to move longitudinally with respect to the base, in turn causing the medical instrument mounting structure to move longitudinally with respect to the base.

* * * * *